US005214620A

United States Patent [19]

Rattner

[11] Patent Number: 5,214,620

[45] Date of Patent: May 25, 1993

[54] ELECTRICALLY DRIVEABLE SHOCKWAVE SOURCE

[75] Inventor: Manfred Rattner, Grossenseebach, Fed. Rep. of Germany

[73] Assignee: Siemens Aktiengesellschaft, Munich, Fed. Rep. of Germany

[21] Appl. No.: 761,396

[22] Filed: Sep. 18, 1991

[30] Foreign Application Priority Data

Sep. 27, 1990 [EP] European Pat. Off. ........ 90118602.3

[51] Int. Cl.[5] .............................................. A61B 17/22

[52] U.S. Cl. .................................... 367/142; 367/175; 367/182; 181/142; 128/24 EL; 128/662.03

[58] Field of Search ............... 367/140, 142, 175, 182, 367/185; 181/142; 128/24 A, 662.03, 660.01, 24 EL

[56] References Cited

U.S. PATENT DOCUMENTS 4,674,505 6/1987 Pauli et al. ........................ 128/24 A
4,793,329 12/1988 Mahler et al. .................... 128/24 A
4,796,608 1/1989 Koehler ............................ 128/24 A
4,924,858 5/1990 Katona ............................... 367/175

*Primary Examiner*—J. Woodrow Eldred
*Attorney, Agent, or Firm*—Hill, Steadman & Simpson

[57] ABSTRACT

An electrically driveable shockwave source for generating acoustic shockwaves of the type suitable for medical therapy, as a coil arrangement and a membrane disposed adjacent the coil arrangement. The membrane and/or the coil arrangement is formed by a multi-layer structure, with each layer having electrically conductive elements therein insulated from each other, in the form of electrically conductive sections in the membrane, or electrically conductive windings connected in parallel in the coil arrangement.

24 Claims, 3 Drawing Sheets

ELECTRICALLY DRIVEABLE SHOCKWAVE SOURCE

BACKGROUND OF THE INVENTION

1. Field of the Invention

The present invention is directed to an electrically driveable shockwave source of the type for generating acoustic shockwaves suitable for medical therapy, and in particular to such a shockwave source having a coil arrangement with a membrane disposed opposite the coil arrangement.

2. Description of the Prior Art

Electrodynamic shockwave sources are used, for example, for medical therapy for the non-invasive disintegration of calculi, for treating pathological tissue conditions, or for the treatment of bone diseases. Such shockwave sources are operated by charging the coil arrangement with a high-voltage pulse. The membrane consists of electrically conductive material, and as a result of the charging of the coil arrangement, currents are induced in the membrane in a direction opposite to the direction of the current flowing in the coil arrangement. As a consequence of the opposing magnetic fields arising due to the opposite flows of respective currents in the coil arrangement and the membrane, repulsion forces are exerted on the membrane causing the membrane to suddenly and rapidly move away from the coil. A pressure pulse is thereby introduced into an acoustic propagation medium adjacent the membrane. The pressure pulse intensifies into a shockwave as it propagates through the medium as a consequence of the non-linear compression properties thereof. In the present discussion, however, the term "shockwave" will always be used, and will encompass within its meaning an incipient shockwave, i.e., a pressure pulse.

If necessary, the shockwave may be concentrated onto a focus zone with suitable focusing means, for example, an acoustic lens, or by appropriate shaping of the shockwave source, for example, fashioning the membrane and the coil in the form of a portion of a sphere.

The shockwave source and the subject to be acoustically irradiated are acoustically coupled to each other in a suitable manner, and are aligned relative to each other so that the region to be acoustically irradiated is situated in the focus zone of the shockwave source.

In order to achieve an optimum conversion of the electrical energy supplied to the shockwave source into acoustic shock energy, it is necessary to attach the membrane as closely as possible to the coil arrangement. In conventional shockwave sources, however, the closeness of the membrane to the coil arrangement is limited due to the difference in potential which exists between the coil arrangement and the membrane. A minimum spacing must be observed in order to avoid voltage arcing. Voltage arcing would deteriorate the operation of the shockwave source, and would lead to damage of the membrane and thus to premature failure thereof. In order to insure an adequate service life of the membrane, the necessary distance which must be maintained between the membrane and the coil arrangement results in an extremely low efficiency in the conversion of electrical energy into acoustic shock energy. Apart from the fact that this is an unsatisfactory circumstance insofar as efficiency, a further disadvantage is that relatively complicated measures for must be undertaken for eliminating the considerable heat which is dissipated due to the low efficiency of the shockwave generation.

The problems of low efficiency and high heat generation are most acute in shockwave sources of the type described above wherein the membrane consists of metal, as described, for example, in U.S. Pat. No. 4,674,505. One proposed solution to these problems is disclosed in European Application 0 266 538, corresponding to U.S. Pat. No. 4,793,329, wherein the membrane consists of an insulator disc on which electrically conductive sections are arranged in the form of concentric rings. This structure creates an insulation path having an extremely long length, which must be overcome before voltage arcing can occur, thereby permitting the membrane to be arranged relatively close to the coil arrangement.

Another electrodynamic shockwave source is disclosed in European Application 0 256 232, corresponding to U.S. Pat. No. 4,796,608, wherein the coil consists of two parallel, superimposed, series-connected layers with one of the layers having a smaller difference in potential with respect to the membrane, and that layer being disposed directly opposite the membrane. Because the voltage at the coil arrangement drops across the coil, a difference in potential is present between the membrane and the layer immediately adjacent thereto, which is lower than the magnitude of the voltage at the coil. The membrane can thus be situated in relatively close proximity to the coil.

Although the risk of voltage arcing is minimized in these known structures, the efficiency is still not entirely satisfactory.

SUMMARY OF THE INVENTION

It is an object of the present invention to provide an electrodynamic shockwave source, of the type having a coil arrangement and a membrane, which has a high energy conversion efficiency without the risk of voltage arcing between the coil arrangement and the membrane. The above object is achieved in a first embodiment of an electrodynamic shockwave source constructed in accordance with the principles of the present invention having a coil arrangement with a membrane disposed opposite the coil arrangement, wherein the membrane is formed by a plurality of electrically conductive sections which are electrically insulated from each other and which are arranged in a plurality of layers. An improved electromagnetic interaction results as a consequence of the arrangement of the electrically conductive sections in a plurality of layers. A high-voltage pulse having a defined peak voltage and pulse shape, which charges the coil arrangement, thus leads to higher repulsion forces in this inventive structure than in the case of a conventional shockwave source without a multi-layer membrane.

The above object is also achieved in a second embodiment of shockwave source constructed in accordance with the principles of the present invention, also having a coil arrangement and a membrane, wherein the membrane contains electrically conductive material and the coil arrangement is formed by a plurality of windings which are electrically insulated from each other and which are connected in parallel, the windings being respectively arranged in a plurality of layers. As used herein with regard to the windings, the phrase "electrically insulated from each other" means that each winding in a layer is electrically insulated from the other windings, except for two electrical connections forming a parallel arrangement of the windings. Similar to the first embodiment, an improved electromagnetic interaction between the coil arrangement and the membrane also occurs in this embodiment, as a result of the layer structure of the coil arrangement.

The above object is also achieved in a third embodiment of an electrodynamic shockwave source constructed in accordance with the principles of the present invention again having a coil arrangement and a membrane disposed opposite the coil arrangement, wherein the membrane is formed by a plurality of electrically conductive sections which are electrically insulated from each other and arranged in a plurality of layers, and wherein the coil arrangement is formed by a plurality of windings electrically insulated from each other and connected in parallel, also arranged in a plurality of layers. In this embodiment, because both the membrane and the coil arrangement have a layered structure, a particularly good electromagnetic interaction results.

The conductive sections of the membrane and the conductive windings of the coil arrangement will be referred to herein generically as conductive elements.

In all of the above embodiments, the improved electromagnetic interaction results due to the creation of a more beneficial curve of the magnetic and electrical field lines which results due to the layered structure. The layered structure causes the generation of a field lines curve having a low scatter. As mentioned above, the improved electromagnetic interaction occurs as result of an enhancement of the repulsion forces arising between the coil arrangement and the membrane, so that an improved efficiency is achieved in the conversion of electrical energy into acoustic shock energy, which does not simultaneously create a risk of voltage arcing.

To achieve an improvement in the electric strength of the shockwave source in any of the above embodiments having a multi-layer membrane, the electrically conductive sections of one layer of the membrane, at least partially overlap the spaces between the electrically conductive sections of at least the immediately adjacent layer of the membrane. A capacitive coupling of the electrically conductive sections to one another is achieved in this manner, with the result that the entire operating voltage of the shockwave source is uniformly divided into differences in potential between the individual electrically conductive sections. The differences in potential which are present between the electrically conductive sections in a single layer, as well as between the electrically conductive sections in adjacent and other layers, are comparatively slight, so that the risk of voltage arcing is substantially suppressed, and a reduction in the distance between the membrane and the coil arrangement, providing the advantage of a further improvement in efficiency, is possible under certain circumstances. An especially good capacitative coupling, and thus particularly uniform differences in potential, can be achieved in any of the above embodiments having a multi-layer membrane, by making the electrically conductive sections in a plurality of successive layers in the form of concentric rings, with the concentric rings of the layers being arranged offset relative to one another, such that the concentric rings of one layer overlap the annular spaces between the concentric rings of the immediately adjacent layer.

A further improvement in efficiency is possible in any of the above embodiments having a multi-layer coil arrangement, by making the turns of the winding of a layer of the coil arrangement at least partially overlap the spaces between the turns of the winding of at least the immediately adjacent layer. This results in the generation of an extremely uniform and low-scatter electromagnetic field, which is reflected in an improvement of the electromagnetic interaction between the coil arrangement and membrane and thus an improvement in efficiency.

A further reduction of the inhomogeneities of the electromagnetic field generated by the coil arrangement and thus a further enhancement in efficiency, can be achieved in any of the multi-layer coil arrangement embodiments by arranging the turns of the windings of a plurality of successive layers in the form of a spiral, with the windings of the layers being offset relative to each other so that the turns of the winding of one layer overlap the spiral space between the turns of the winding of the immediately adjacent layer. The multi-layer membrane can also be constructed in the same manner.

In a preferred embodiment of the invention, an electrically conductive coating is provided at that side of the membrane facing away from the coil arrangement, the electrically conductive coating being insulated from the electrically conductive sections. By connecting the coating to a shielding potential, for example ground potential, an effective shielding of the shockwave source is achieved. This provides the advantage that undesired influences on neighboring electronic devices and lines, due to the electromagnetic disturbances emitted by the shockwave source, are substantially reduced.

DESCRIPTION OF THE PREFERRED EMBODIMENTS

Figure 1:
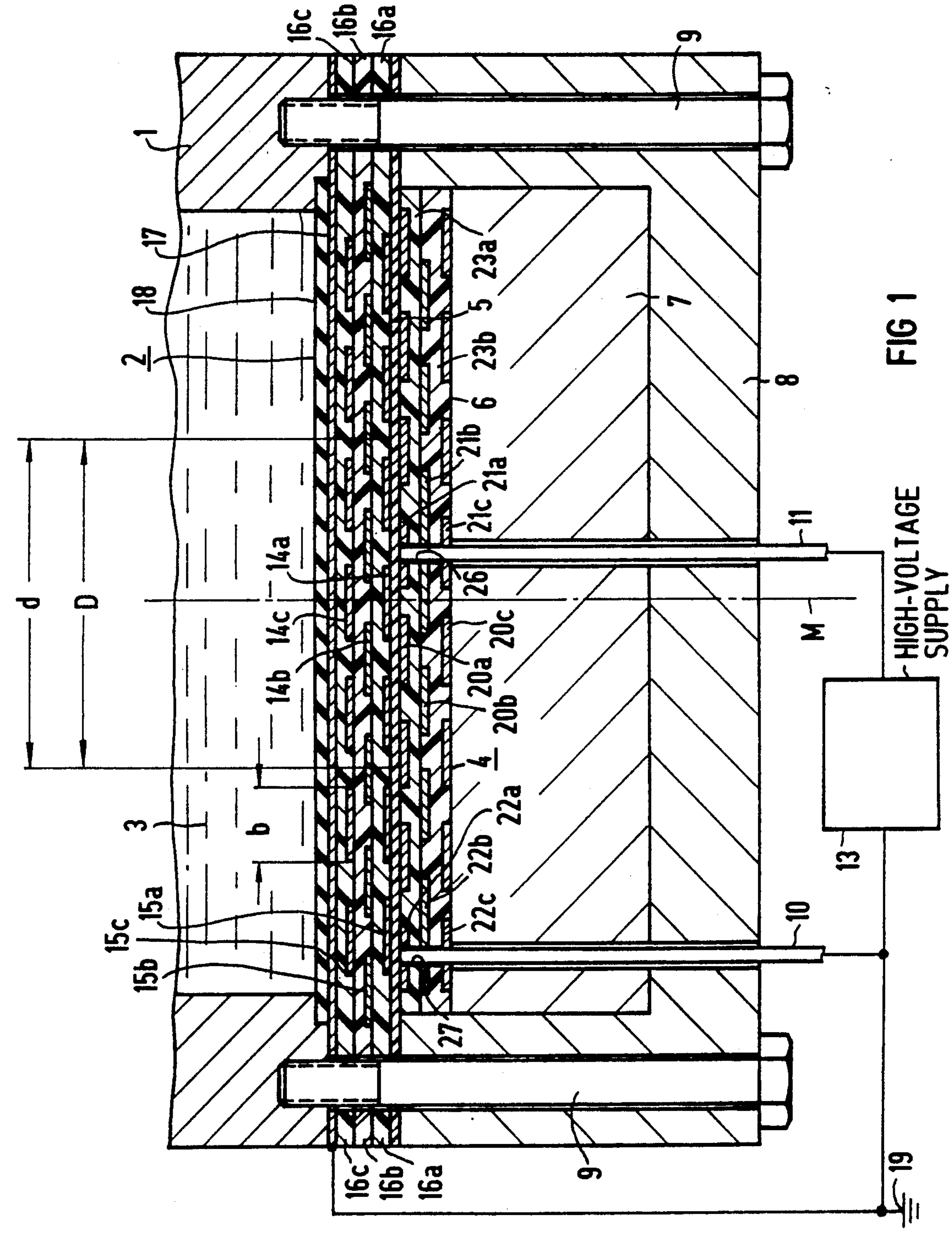
FIG. 1 is a side sectional view through a shockwave source constructed in accordance with the principles of the present invention.

A shockwave source as shown in FIG. 1, constructed in accordance with the principles of the present invention, includes an approximately tubular housing 1 (only partially shown) containing a volume 3 filled with a fluid functioning as an acoustic propagation medium for the shockwaves. The housing 1 is terminated at one end by a membrane 2. A coil arrangement 4 having spiral turns is disposed opposite the membrane 2. The membrane 2 contains electrically conductive material, and an insulating foil 5 is disposed between the membrane 2 and the coil arrangement 4.

The coil arrangement 4 is disposed on a seating surface 6 of an insulator 7 which is received in a cap 8. The membrane 2, the insulating foil 5 and the cap 8 containing the insulator 7 with the coil arrangement 4 are secured to the housing 1 with bolts 9. The coil arrangement 4 is affixed to the seating surface 6 of the insulator 7 by gluing. The, coil arrangement 4 is connected to a schematically shown high-voltage supply 13 via conductors 10 and 11, which extend through bores in the insulator 7 and the cap 8 to the exterior of the shockwave source. The high-voltage supply 13 charges the coil arrangement 4 with high-voltage pulses. As a consequence of the pulse-like currents which are thereby caused to flow through the coil arrangement 4, the membrane 2 is suddenly repelled from the coil arrangement 4, leading to the formation of a shockwave in the fluid in the volume 3.

The membrane 2 is a multi-layer structure containing conductive elements in the form of a plurality of electrically conductive sections insulated from each other and arranged in a plurality of layers. The exemplary embodiment of FIG. 1 has three layers. For clarity, only the innermost and outermost electrically conductive sections of the individual layers are provided with reference symbols in FIGS. 1 and 2. The innermost electrically conductive sections are 14*a*, 14*b* and 14*c*, and the outermost electrically conductive sections are 15*a*, 15*b* and 15*c*. The electrically conductive sections 14*a* and 15*a* are contained in the layer of the membrane 2 which is immediately adjacent the coil arrangement 4. The corresponding electrically conductive sections in the layers farthest from the coil arrangement 4 are 14*c* and 15*c*. The respective innermost sections 14*a* and 14*c* of the layers immediately adjacent to, and farthest from, the coil arrangement 4 are circular. All of the other coil sections are in the form of concentric rings having substantially the same width b, arranged with reference to the center axis M of the shockwave source. The conductive sections of the individual layers are offset relative to each other so that the concentric rings of one layer completely overlap the annular spaces between the conductive sections of the immediately adjacent layer. In the illustrated exemplary embodiment, the arrangement of the layers is selected so that the average diameter of an annular space between the conductive sections corresponds to the average diameter of the conductive section overlapping that annular space, as shown by the average diameters d and D in FIG. 1 for a space and for a conductive section, by example. The conductive sections are formed of metal foil, for example copper foil or silver foil, and are attached, for example by gluing, to the side of respective insulator foils 16*a*, 16*b* and 16*c* facing the coil arrangement 4.

The individual layers, formed by the insulator foils 16*a*, 16*b* and 16*c* are joined to each other, for example by gluing, in a planar format. That side of the insulator foil 16*c* facing away from the coil arrangement 4 is provided with an electrically conductive coating 17, for example a metal foil, which substantially covers the entire insulator foil 16*c*. The coating 17 is electrically insulated from the conductive sections by the insulator foil 16*c*, and has a layer 18 of a cavitation-resistant material, for example rubber, facing toward the acoustic propagation medium. The layer 18 can be joined to the coating 17, for example, gluing. The coating 17 is connected to a shielding potential, such as ground potential 19, with one terminal of the high-voltage supply 13 also being at ground potential in the exemplary embodiment of FIG. 1.

In the embodiment of FIG. 1, the coil arrangement 4 is also a multi-layer structure, having conductive elements in the form of a plurality of windings 20*a*, 20*b* and 20*c* which are electrically insulated from one another and are connected in parallel. The windings are arranged in a corresponding plurality of layers, i.e., three layers. For clarity, only the innermost and outermost turns of the windings 20*a*, 20*b* and 20*c* are provided with reference symbols in FIGS. 1 and 3. The innermost turns are designated 21*a*, 21*b* and 21*c*, and the outermost turns are designated 22*a*, 22*b* and 22*c*. The winding 20*a* is the immediately adjacent the membrane 2. The winding 20*c* is farthest from the membrane 2. All turns of the windings 20*a*, 20*b* and 20*c* of the individual layers are offset relative to each other so that turns of the winding of one layer completely overlap the spiral space between the turns of the winding of the immediately adjacent layer. In the exemplary embodiment of FIG. 1, the arrangement of the layers is selected so that, at arbitrary locations in the coil arrangement 4, the average radius of curvature of the respective spiral space corresponds to the average radius of curvature of the turn overlapping that space, as shown, as an example, by the average radii of curvature r and R in FIG. 3 at one location of the coil arrangement 4. The turns of the individual windings 20*a*, 20*b* and 20*c* are formed by metal foil, for example copper foil or silver foil. The windings 20*a* and 20*b* are attached to that side of respective insulator foils 23*a* and 23*b* facing toward the membrane 2. The winding 20*c* is applied on that side of the insulator layer 23*b* facing away from the membrane 2. The windings 20*a*, 20*b* and 20*c* may be connected to the insulator layers 23*a* and 23*b* by, for example, gluing. The insulator layers 23*a* and 23*b* having the respective windings 20*a*, 20*b* and 20*c* are joined to each other by gluing in a planar format. The entire coil arrangement 4 is mounted in a planar fashion in the seating surface 6 of the insulator 7, for example by gluing.

The windings 20*a*, 20*b* and 20*c* of the coil arrangement 4 are connected in parallel. To this end, the innermost turns 21*a*, 21*b* and 21*c* of the windings 20*a*, 20*b* and 20*c* are respectively provided with contact pads 24*a*, 24*b* and 24*c*, and the outermost turns 22*a*, 22*b* and 22*c* of the windings 20*a*, 20*b* and 20*c* are respectively provided with contact pads 25*a*, 25*b* and 25*c*. The innermost contact pads are each penetrated by a bore 26 and the outermost contact pads are each penetrated by a bore 27, so that the pads are "through-connected" in a manner known from printed circuit board technology, so that the windings 20*a*, 20*b* and 20*c* are electrically connected to each other in the respective regions of the innermost and outermost contact pads. The lines 10 and 11 are respectively soldered into the bores 27 and 26.

Figure 2:
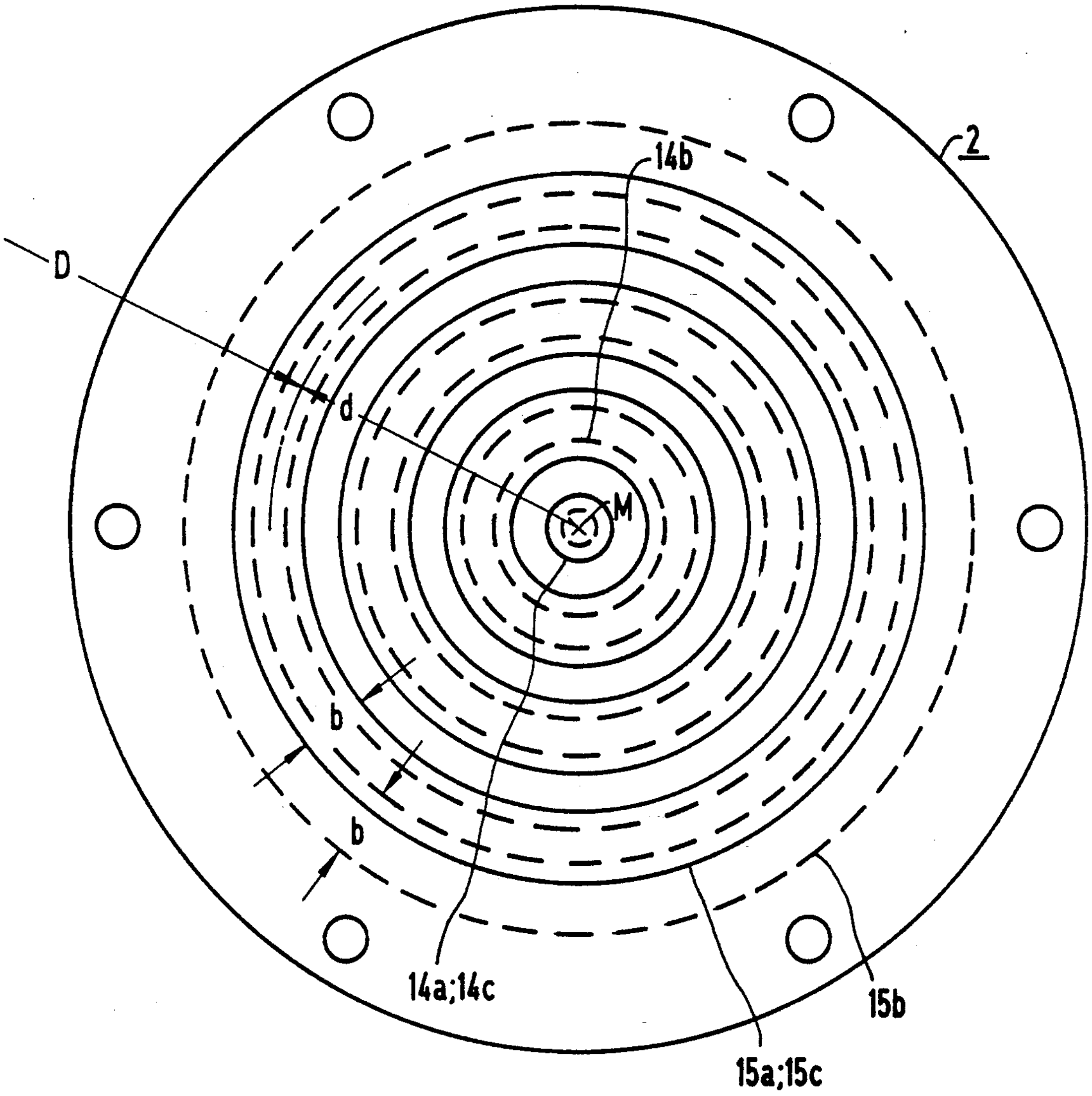
FIG. 2 is a plan view of the membrane of the shockwave source of FIG. 1.

The windings 20*a* and 20*c* are congruently arranged in the exemplary embodiment. This can be seen in FIG. 3, which is a view of that side of the coil arrangement 4 facing the membrane 2. The winding 20*a*, illustrated with solid lines, is also provided with a reference symbol identifying the winding 20*c*. In an analogous manner, the electrically conductive sections of the layer of the membrane 2 immediately adjacent the coil arrangement 4, and the layer of the membrane 2 farthest from the coil arrangement 4, are congruently arranged. This is illustrated in FIG. 2, which shows a view of that side of the membrane 2 facing toward the coil arrangement 4. The conductive sections 14*a* and 15*a* illustrated with solid lines in the layer of the membrane immediately adjacent the coil arrangement 4 are also provided with the reference symbols 14*c* and 15*c* identifying the layer farthest from the coil arrangement 4. If more than three layers are provided, it is recommended to arrange the conductive sections or windings of the individual layers so that the conductive sections or windings of the odd-numbered layers are arranged congruently with each other, and the electrically conductive sections or windings of the even-numbered layers are congruently arranged relative to each other.

Figure 3:
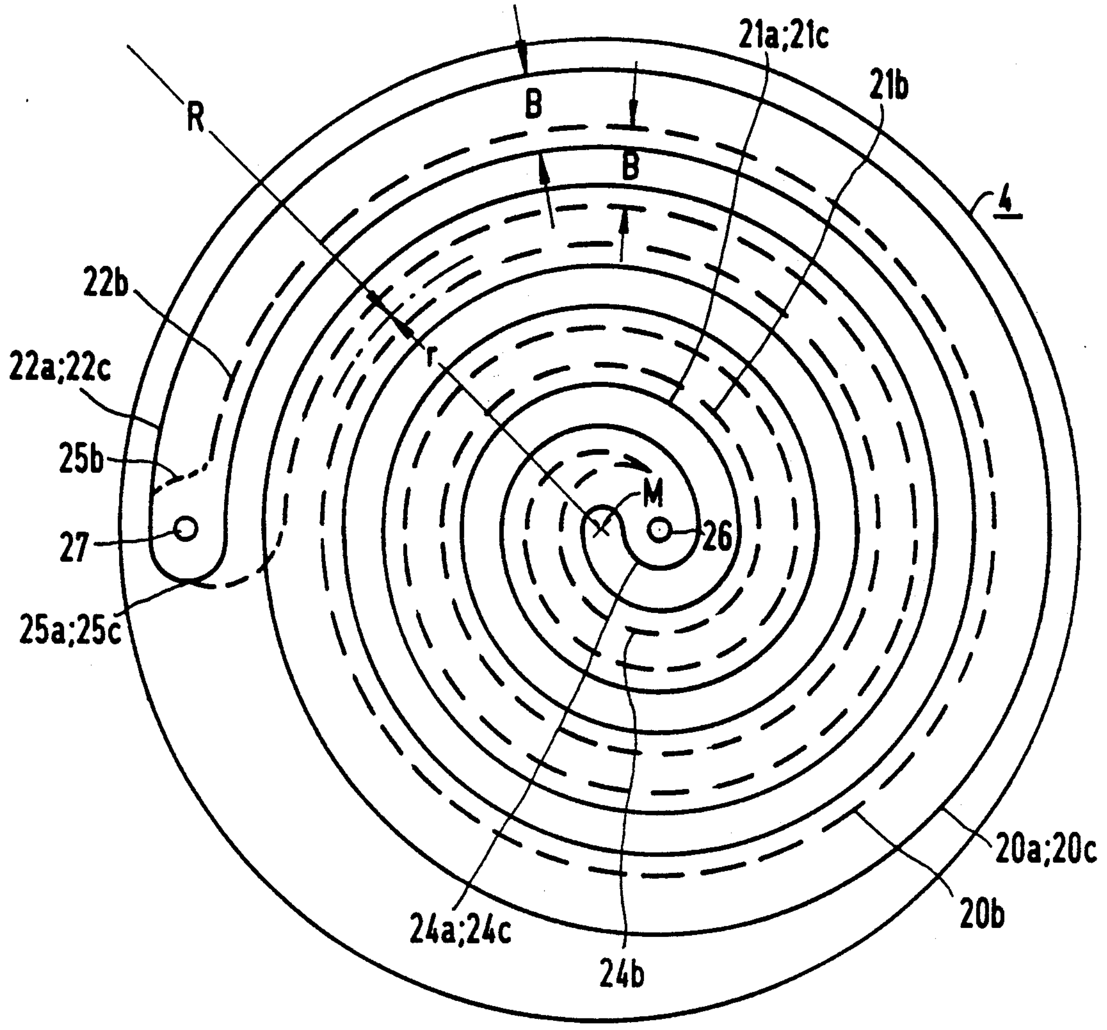
FIG. 3 is a plan view of the coil arrangement of the shockwave source of FIG. 1.
Figure 4:
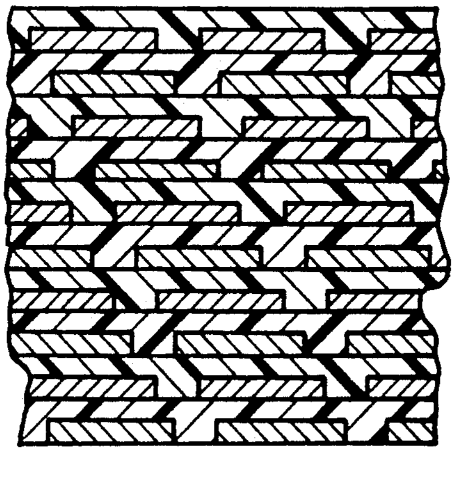
FIG. 4 is a side sectional view of a portion of a further embodiment of either a membrane or a coil arrangement for use in shockwave source constructed in accordance with the principles of the present invention.

As an alternative to the arrangement shown in FIGS. 1–3, it is possible to arrange the conductive sections or windings of the individual layers so that the conductive sections, or the turns of a winding, of one layer only partially overlap the spaces between the conductive sections, or the turns of a winding, of the immediately adjacent layer. Such an alternative arrangement is shown in FIG. 4, which can represent either a multi-layer membrane or a multi-layer coil arrangement. In the embodiment shown in FIG. 4, the spaces between the conductive sections, or winding turns, of a layer are overlapped by the conductive sections, or winding turns, of the layer immediately following the adjacent layer, in other words, there is one layer in between. A coincidence of the mean diameters d and D in the case of conductive sections of the membrane, or of the radii of curvature r and R in the case of winding turns of the coil arrangement, is established in the embodiment FIG. 4 for the first and fifth layers, the second and sixth layers, the third and seventh layers, etc. A congruent arrangement of the conductive sections or the windings would be established for the first and ninth layers, for the second and tenth layers, for the third and eleventh layers, etc.

Due to the layered structure of the membrane 2 and the coil arrangement 4, a beneficial, particularly a low-scatter, curvature of the magnetic and electric field lines is achieved. An improved electromagnetic interaction between the coil arrangement 4 and the membrane 2 results therefrom, achieving an improved efficiency in the conversion of electrical energy into acoustic energy. A further improvement in the electromagnetic interaction, and thus, in the efficiency, is achieved by the turns of the windings 20*a*, 20*b* and 20*c* of the coil arrangement 4 overlapping in the described manner, since this leads to an extremely uniform electromagnetic field. Another improvement in the efficiency, and thus in the service life, of the membrane 2 is achieved by the electrically conductive sections of the membrane 2 overlapping as described. This achieves a capacitative coupling of the conductive sections to one another, resulting in uniformly divided differences in potential being present betwen the individual conductive sections, so that the risk of voltage arcing is substantially suppressed. A uniform distribution of the differences in potential can be further promoted by the presence of an electrically conductive connection (not shown) between the conductive section 14*a* to the conductor 11, and between the conductive section 15*a* and the conductor 10.

The thicknesses of the conductive sections, of the insulator foils 16*a*, 16*b* and 16*c*, of the coating 17, of the layer 18, of the windings 20*a*, 20*b* and 20*c* and of the insulator layers 23*a* and 23*b* are shown greatly exaggerated in FIGS. 1 and 4 for clarity. The conductive sections and the windings are shown as being contained in the respective insulator foil or insulator layer in such a manner that a planar surface is maintained. Such planar surfaces need not necessarily be maintained in the case of a practical embodiment of the shockwave source, however, because the thickness of the conductive sections, and of the windings can be extremely small, for example less than $10^{-4}$ m. In this case, the adhesive layers (which are not shown in the drawings) provided for joining the individual layers can provide the necessary compensation to accommodate such nonplanar surfaces. The individual layers, moreover, can be produced photochemically, similar to a printed circuit, in the form of an electrically conductive layer, for example a copper layer, and a laminated electrically insulating plastic foil or layer.

As a consequence of the connection of the coating 17 to ground potential 19 as a shielding potential, an effective shielding of the shockwave source is achieved, so that disturbances emitted by the shockwave source are substantially reduced. This effect is further promoted if the housing 1 consists of an electrically conductive material, and is also at ground potential 19 as a consequence of being in contact with the coating 17.

In the above exemplary embodiment, both the membrane 2 and the coil arrangement 4 are shown as multi-layer structures, however, it is within the scope of the inventive concept disclosed herein to provide a shockwave source wherein only the membrane 2 is a multi-layer structure, or wherein only the coil arrangement 4 is a multi-layer structure.

Additionally, in the exemplary embodiment shown in the drawings, the conductive sections of the individual layers, and the windings 20*a*, 20*b* and 20*c* of the individual layers, are arranged in planar surfaces which are parallel to each other. It is also possible, for example, to arrange these components to form spherically curved surfaces instead of planar surfaces, resulting in a shockwave source having a membrane and a coil arrangement which are spherically curved in a known manner.

Although further modifications and changes may be suggested by those skilled in the art, it is the intention of the inventor to embody within the patent warranted hereon all changes and modifications as reasonably and properly come within the scope of his contribution to the art.

I claim as my invention:

1. An electrodynamic acoustic shockwave source comprising:
   - a housing containing an acoustic propagation medium:
   - a membrane containing electrically conductive material disposed in said housing adjacent said acoustic propagation medium;
   - coil means disposed in said housing for causing said membrane to be rapidly repelled from said coil means to generate an acoustic shockwave in said propagation medium when said coil means is charged with a current pulse; and
   - at least one of said membrane or said coil means containing a plurality of electrically conductive elements which are insulated from each other and which are disposed in a plurality of layers with more than one electrically conductive element per layer, the electrically conductive elements in each layer being arranged with spaces therebetween, and the electrically conductive elements of a layer at least partially overlapping the spaces in an adjacent layer.

2. An electrodynamic acoustic shockwave source as claimed in claim 1 wherein said electrically conductive elements in said layers are arranged in a plurality of parallel surfaces.

3. An electrodynamic acoustic shockwave source as claimed in claim 2 wherein said surfaces are planar.

4. An electrodynamic acoustic shockwave source as claimed in claim 1 further comprising an electrically conductive coating disposed on a side of said membrane facing away from said coil means electrically insulated from said membrane, and connected to a source of shielding potential.

5. An electrodynamic acoustic shockwave source comprising:

a housing containing an acoustic propagation medium;

a membrane disposed in said housing adjacent said acoustic propagation medium and consisting of a plurality of electrically conductive sections which are insulated from each other and which are disposed in a plurality of layers with at least one layer having more than one electrically conductive section therein; and coil means disposed in said housing for causing said membrane to be rapidly repelled from said coil means to generate an acoustic shockwave in said propagation medium when said coil means is charged with a current pulse.

6. An electrodynamic acoustic shockwave source as claimed in claim 5 wherein each of said layers has more than one electrically conductive section therein, said electrically conductive sections in each layer of said membrane being arranged with spaces therebetween, and the electrically conductive sections in a layer at least partially overlapping the spaces in an adjacent layer.

7. An electrodynamic acoustic shockwave source as claimed in claim 6 wherein each layer of said membrane includes a plurality of concentric rings forming said electrically conductive sections, separated by annular spaces, and wherein said concentric rings in successive layers are disposed offset relative to each other so that the concentric rings of a layer overlap the annular spaces of an adjacent layer.

8. An electrodynamic acoustic shockwave source as claimed in claim 5 wherein said electrically conductive sections in said layers of said membrane are arranged in a plurality of parallel surfaces.

9. An electrodynamic acoustic shockwave source as claimed in claim 8 wherein said surfaces are planar.

10. An electrodynamic acoustic shockwave source as claimed in claim 5 further comprising an electrically conductive coating disposed on a side of said membrane facing away from said coil means and electrically insulated from said membrane, and connected to a source of shielding potential.

11. An electrodynamic acoustic shockwave source comprising:

a housing containing an acoustic propagation medium;

a membrane containing electrically conductive material disposed in said housing adjacent said acoustic propagation medium; and coil means disposed in said housing for causing said membrane to be rapidly repelled from said coil means to generate an acoustic shockwave in said propagation medium when said coil means is charged with a current pulse, said coil means consisting of a plurality of electrically conductive windings connected in parallel and respectively disposed in a plurality of layers with each winding in a layer being insulated from the windings in all other layers in said plurality of layers.

12. An electrodynamic acoustic shockwave source as claimed in claim 11 wherein each winding in each layer of said coil means has a plurality of turns arranged with a space therebetween, and wherein the turns of a winding in a layer of said coil means at least partially overlap the space in an adjacent layer.

13. An electrodynamic acoustic shockwave source as claimed in claim 12 wherein said winding in each layer of said coil means is a spiral formed by said plurality of winding turns and wherein said space is a spiral space between said winding turns, and wherein said windings in successive layers of said coil means are arranged offset relative to each other so that the winding turns of a layer overlap the spiral space in an adjacent layer.

14. An electrodynamic acoustic shockwave source as claimed in claim 11 wherein said electrically conductive windings in said layers of said coil means are arranged in a plurality of parallel surfaces.

15. An electrodynamic acoustic shockwave source as claimed in claim 14 wherein said surfaces are planar.

16. An electrodynamic acoustic shockwave source as claimed in claim 11 further comprising an electrically conductive coating disposed on a side of said membrane facing away from said coil means and electrically insulated from said membrane, and connected to a source of shielding potential.

17. An electrodynamic acoustic shockwave source comprising:

a housing containing an acoustic propagation medium;

a membrane disposed in said housing adjacent said acoustic propagation medium and consisting of a plurality of electrically conductive sections insulated from each other and respectively disposed in a plurality of membrane layers; and coil means disposed in said housing for causing said membrane to be rapidly repelled from said coil means to generate an acoustic shockwave in said propagation medium when said coil means is charged with a current pulse, said coil means consisting of a plurality of electrically conductive windings connected in a parallel and respectively disposed in a plurality of coil means layers with each winding in a coil means layer being insulated from the windings in all other coil means layers in said plurality of coil means layers.

18. An electrodynamic acoustic shockwave source as claimed in claim 17 wherein at least two adjacent ones of said plurality of membrane layers each contain more than one electrically conductive sections, said electrically conductive sections in each, of said adjacent membrane layers being arranged with spaces therebetween, and the electrically conductive sections in a one of said adjacent membrane layers at least partially overlapping the spaces in the other of said adjacent membrane layers.

19. An electrodynamic acoustic shockwave source as claimed in claim 18 wherein each membrane layer includes a plurality of concentric rings forming said electrically conductive sections, separated by annular spaces, and wherein said concentric rings in successive membrane layers are disposed offset relative to each other so that the concentric rings of a membrane layer overlap the annular spaces of an adjacent membrane layer.

20. An electrodynamic acoustic shockwave source as claimed in claim 17 wherein each winding in each coil means layer has a plurality of turns arranged with a space therebetween, and wherein the turns of a winding in a coil means layer at least partially overlap the space in an adjacent coil means layer.

21. An electrodynamic acoustic shockwave source as claimed in claim 20 wherein said winding in each coil means layer is a spiral formed by said plurality of winding turns and wherein said space is a spiral space between said winding turns, and wherein said windings in successive coil means layers are arranged offset relative to each other so that the winding turns of a coil means layer overlap the spiral space in an adjacent coil means layers.

22. An electrodynamic acoustic shockwave source as claimed in claim 17 wherein said electrically conductive elements in said membrane layers and said electrically conductive windings in said coil means layers are arranged in a plurality of parallel surfaces.

23. An electrodynamic acoustic shockwave source as claimed in claim 22 wherein said surfaces are planar.

24. An electrodynamic acoustic shockwave source as claimed in claim 17 further comprising an electrically conductive coating disposed on a side of said membrane facing away from said coil means and electrically insulated from said membrane, and connected to a source of shielding potential.

* * * * *